(12) United States Patent
Okawauchi

(10) Patent No.: US 6,337,488 B1
(45) Date of Patent: Jan. 8, 2002

(54) DEFECT INSPECTION APPARATUS AND DEFECT INSPECTION METHOD

(75) Inventor: Kouki Okawauchi, Kanagawa (JP)

(73) Assignee: Sony Corporation (JP)

( * ) Notice: Subject to any disclaimer, the term of this patent is extended or adjusted under 35 U.S.C. 154(b) by 0 days.

(21) Appl. No.: 09/515,672

(22) Filed: Feb. 29, 2000

(30) Foreign Application Priority Data

Mar. 2, 1999 (JP) ............................................. 11-054128

(51) Int. Cl.[7] .............................................. G01N 21/86
(52) U.S. Cl. ............................. 250/559.05; 250/370.08; 250/336.2; 250/368
(58) Field of Search ..................... 438/14, 15; 435/7.92; 356/402, 349; 359/629

(56) References Cited

U.S. PATENT DOCUMENTS 5,781,294 A * 7/1998 Nakata ........................ 365/349
6,084,716 A * 7/2000 Sanada ........................ 359/629

* cited by examiner

Primary Examiner—John F. Niebling
Assistant Examiner—Andre' C Stevenson
(74) Attorney, Agent, or Firm—Rader, Fishman & Grauer PLLC; Ronald P. Kananen

(57) ABSTRACT

A defect inspection apparatus enabling more reliable and quicker detection of a defect present in the surface of a stacked film formed on a wafer and enabling reliable and quicker detection of a minute defect even if there is unevenness in the surface of the wafer, including a light source, a light frequency shifter unit for converting light from the light source to a plurality of beams of inspection light and a beam of reference light having close frequencies, an object lens upon which the beams of inspection light are incident and focusing the beams of light on the wafer to form a plurality of different focal points corresponding to the beams of inspection light, a laser scanning unit for making the beams of inspection light scan the wafer, a light detection unit and cofocal pinhole plate 13 for detecting an intensity of a superposed light of the beams of reflected light and the beam of reference light at a cofocal point, and an analyzing unit serving as a contrast waveform generating means for generating and combining contrast waveforms in the scanning direction at focal positions based on the light intensity detected by the optical detection unit and defect inspection method.

20 Claims, 6 Drawing Sheets

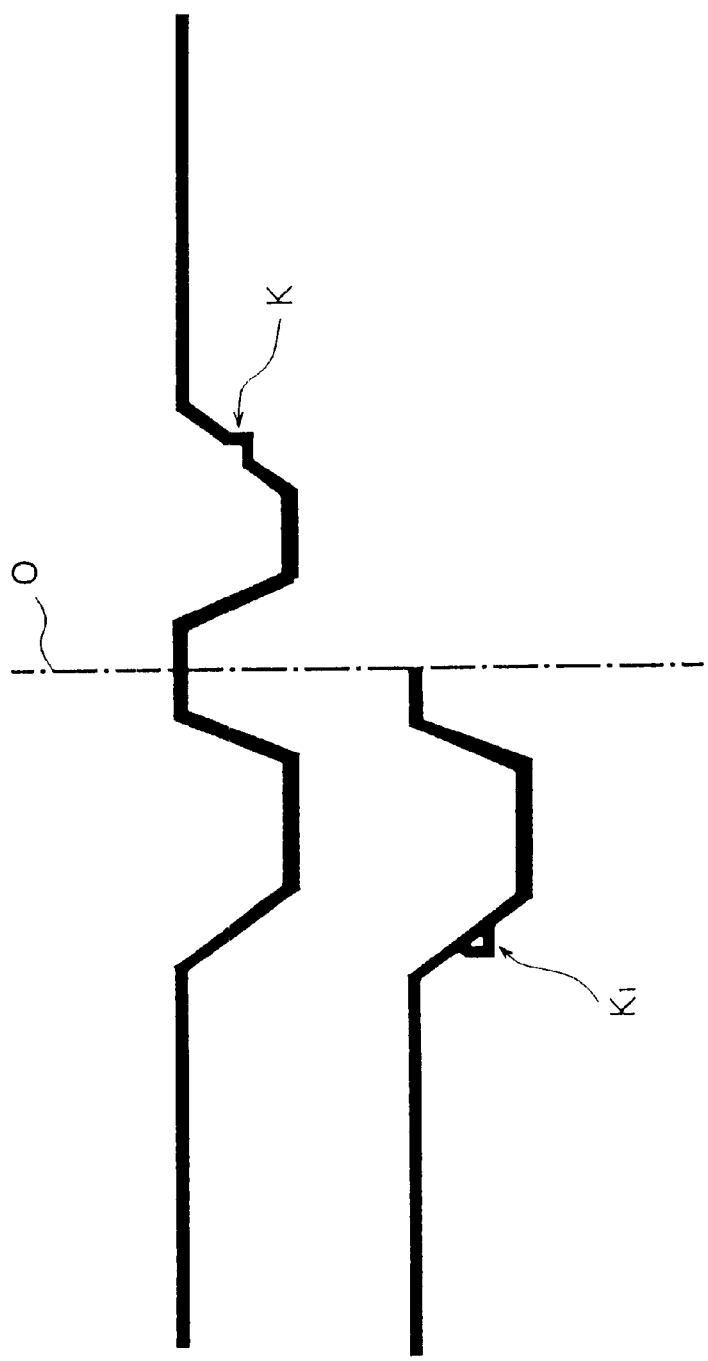

DEFECT INSPECTION APPARATUS AND DEFECT INSPECTION METHOD

BACKGROUND OF THE INVENTION

1. Field of the Invention

The present invention relates to a defect inspection apparatus and a defect inspection method suitable for inspection of scratches, dust, and other defects present in a pattern formed in films in a process of manufacture of a semiconductor device having for example a stacked film structure.

2. Description of the Related Art

Up to the present, inspection of scratches present in a pattern on a semiconductor wafer, dust adhering to the pattern, and other defects in the process of manufacture of a semiconductor device has been carried out by taking the image of the semiconductor wafer creating a contrast waveform from the two dimensional image and detecting the same.

FIG. 5 is a view schematically showing principal parts of an example of the configuration of a defect inspection apparatus for inspection of scratches present in a pattern on a semiconductor wafer, dust adhering to the pattern, and other defects.

The defect inspection apparatus shown in FIG. 5 is configured so as to emit a beam of visible light from a lamp 101 via a lens 102, a half mirror 103, and an object lens 104 onto a semiconductor wafer W and to receive the beam of reflected light via the object lens 104, the half mirror 103, and an image-forming lens 105 at a camera 106.

In the defect inspection apparatus having the above configuration, the beam of light reflected from the semiconductor wafer W passes through the object lens 104, half mirror 103, and image-forming lens 105 to be received at the camera 106, a contrast waveform reflecting the surface shape of the semiconductor wafer W is created based on an intensity of the light received by the camera 106, and the defect present in a pattern formed on the semiconductor wafer W is detected from this contrast waveform by the naked eye or the like.

FIG. 6A is a sectional view in the process of manufacture of a semiconductor device having the stacked film structure as an object to be inspected by the defect inspection apparatus, while FIG. 6B is an example of the contrast waveform of the surface shape of the semiconductor device shown in FIG. 6A by the defect inspection apparatus.

In the structure of the semiconductor device shown in FIG. 6A, for example, a silicon oxide pattern SP is formed on the wafer W, and an aluminum interconnection pattern AP is formed on this silicon oxide pattern SP.

As will be understood from FIGS. 6A and 6B, the contrast waveform at a step difference between the resist pattern RP and the aluminum interconnection pattern AP has a different shape from the actual shape due to the coverage of the aluminum.

Summarizing the problem to be solved by the invention, the shape of the step difference present between the resist pattern RP and the aluminum interconnection pattern AP cannot be accurately determined from a region PA and a region Pr of the contrast waveform obtained by the defect inspection apparatus.

In the defect inspection apparatus, when there is a relatively deep and inclined step difference in the pattern like the inclined surfaces of the resist pattern RP and the aluminum interconnection pattern AP, there is a disadvantage that even if there is for example a scratch, adhesion of dust, or another defect in these inclined surfaces, it cannot be detected.

In the related art, when there is a relatively deep and inclined step as described above in the pattern stacked on the semiconductor wafer, for example a scanning electron microscope (SEM) has been used to conduct a sampling inspection from among a large number of semiconductor wafers.

In defect inspection using a scanning electron microscope, however, the number of the scanning electron microscopes which can be introduced is limited from the viewpoint of the plant and apparatus investment since scanning electron microscopes are high in cost. Further, the number of the semiconductor wafers inspected is limited since the throughput of the inspection is low.

Semiconductor wafers not inspected for defects are sent to the next step. These uninspected semiconductor wafers have become a cause of reduction of the yield of the product.

In the future, in the process of manufacture of a semiconductor device, along with the miniaturization of the circuit pattern of integrated circuits, employment of a stacked film structure of more layers for the semiconductor device cannot be avoided, so development of a defect inspection apparatus which can correctly inspect minute defects existing in a semiconductor wafer in the process of manufacture of a semiconductor device at a low cost and with a high throughput has become necessary.

SUMMARY OF THE INVENTION

An object of the present invention is to provide a defect inspection apparatus and a defect inspection method capable of more reliably and quickly detecting defects existing in patterns formed in the stacked films formed on a wafer in for example a process of manufacture of a semiconductor device, more particularly capable of reliably and quickly detecting minute defects even if there are step differences and other unevenness at the surface of the wafer.

According to a first aspect of the present invention, there is provide a defect inspection apparatus for inspecting for a defect existing in a inspected surface, comprising a light source for emitting a beam of light of a predetermined frequency band, a light frequency changing means for receiving as its input the is beam of light emitted from the light source and outputting the related beam of light converted to a plurality of beams of inspection light having close frequencies different from each other and a beam of reference light beam, a light focusing means upon which the beams of inspection light output from the light frequency changing means are incident through an identical optical path and focusing the related beams of inspection light to the inspected surface to forming a plurality of different focal points corresponding to the beams of inspection light, a scanning means for scanning the focused beams of inspection light on the inspected surface, a superposing means for superposing the beam of the reflected light of the inspection light from the inspected surface and the beam of reference light to cause interference between the beams of reflected light and the beam of reference light, a light receiving means upon which the superposed light of the beams of reflected light and the beam of reference light is incident and detecting the intensity of the superposed light by confocal detection, and a contrast waveform generating means for generating contrast waveforms in the scanning direction at the focal positions in respect to the light intensity detected by the light receiving means and combining the contrast waveforms.

Preferably, the apparatus further comprises a defect detecting means for detecting defects of the pattern based on the contrast waveforms.

Preferably, the light receiving means has a light receiving element for receiving the superposed light and a pin hole plate provided in an incident light path of the superposed light to the light receiving element and having a small aperture and detecting the intensity of the superposed light by confocal detection.

Preferably, the light source selectively output a beam of visible laser light of a visible band and a beam of far-ultraviolet laser light of a far-ultraviolet band.

Preferably, the superposing means has beam splitters for reflecting the beam of reference light output from the light frequency changing means to the light receiving means, passing the beams of reflected light from the inspected surface striking it after following an identical optical path as that for the beams of inspection light, and exposing the same to the light receiving means.

Preferably, the light frequency shifting means has a plurality of acousto-optic modulating means for changing the frequency of the light emitted from the light source by supersonic waves of different frequencies from each other.

Preferably, the inspected surface comprises uneven surface.

Preferably, the inspected surface comprises the surface of a film stacked on a semiconductor substrate and formed into a predetermined pattern.

More preferably, the patterns are formed symmetrical about a predetermined center line, and the defect detecting means detects a part which is not symmetrical about the center line in the contrast waveform data obtained by the contrast waveform generating means as a defect.

Preferably, the scanning means has a galvanomirror or a supersonic light polarization element for scanning the beams of inspection light on the inspected surface.

Preferably, the scanning means two-dimensionally scans the beams of inspection light on the inspected surface, and the contrast waveform generating means generates a contrast image reflecting a three-dimensional shape of the inspected surface from the combined contrast waveforms obtained as a result of the scannings.

According to a second aspect of the present invention, there is provided a defect inspection apparatus for inspecting for a defect present in an inspected surface, comprising a light source for emitting a beam of light of a predetermined frequency band, a light frequency changing means for receiving as its input the beam of light emitted from the light source and outputting the related beam of light converted to a plurality of beams of inspection light and a beam of reference light beam having close frequencies different from each other, a light focusing means upon which the beams of inspection light output from the light frequency changing means are incident through an identical optical path and focusing the related beams of inspection light to the inspected surface to form a plurality of different focal points corresponding to the beams of inspection light, a scanning means for making the focused beams of inspection light scan the inspected surface, a superposing means for superposing beams of reflected light of the beams of inspection light from the inspected surface and the beam of reference light on each other to cause interference between the related beams of reflected light and the beam of reference light, a light receiving means upon which the superposed light of the beams of reflected light and the beam of reference light is incident and detecting the intensity of the superposed light, a contrast waveform generating means for generating contrast waveforms in the scanning direction at the focal positions based on the light intensity detected by the light receiving means and combining the contrast waveforms, and a defect detecting means for detecting a defect of a pattern based on the contrast waveforms.

Preferably, the inspected surface comprises the surface of a film stacked on a semiconductor substrate and formed into a predetermined pattern.

Preferably, the patterns are formed symmetrical about a predetermined center line and the defect detecting means detects a part which is not symmetrical about the center line in the contrast waveform data obtained by the contrast waveform generating means as a defect.

According to a third aspect of the present invention, there is provided a defect inspection apparatus for inspecting for a defect present in an inspected surface, comprising a light source for emitting a beam of light of a predetermined frequency band, a light frequency changing means for receiving as its input the beam of light emitted from the light source and outputting the related beam of light converted to a plurality of beams of inspection light and a beam of reference light beam having close frequencies different from each other, a light focusing means for focusing the related beams of inspection light output from the light frequency changing means on the inspected surface to form focal points, a scanning means for scanning the focused beams of inspection light on the inspected surface, a superposing means for superposing the beam of reflected light of the beams of inspection light from the inspected surface and the beam of reference light on each other to cause interference between the beams of reflected light and the beam of reference light, a light receiving means upon which the superposed light of the beams of reflected light and the beam of reference light is incident and detecting the intensity of the superposed light by confocal detection, and a contrast waveform generating means for generating contrast waveforms in the scanning direction at the focal positions based on the light intensity detected by the light receiving means.

Preferably, the apparatus further comprises a defect detecting means for detecting defects of the pattern based on the contrast waveforms.

Preferably, the inspected surface comprises the surface of a film stacked on a semiconductor substrate and formed into a predetermined pattern.

More preferably, the patterns are formed symmetrical about a predetermined center line, and the defect detecting means detects a part which is not symmetrical about the center line in the contrast waveform data obtained by the contrast waveform generating means as a defect.

Preferably, the light receiving means has an aperture plate having a small aperture for detecting the intensity of the superposed light by confocal detection in the incident optical path of the superposed light.

According to a fourth aspect of the present invention, there is provided a defect inspection method for inspecting for a defect present in an inspected surface, comprising converting light of a predetermined frequency band to a plurality of beams of inspection light and a beam of reference light having close frequencies different from each other, passing the plurality of beams of inspection light through the identical optical path and focusing them on the inspected surface to form a plurality of different focal points corresponding to the beams of the inspection light and scanning them the inspected surface, superposing the beams of reflected light of the beams of inspection light from the inspected surface and the beam of reference light on each other to cause interference between them and detecting the intensity of the related superposed light at the confocal point, generating contrast waveforms in the scanning direction at the focal positions based on the detected light intensity, combining the contrast waveforms, and detecting a defect of the inspected surface based on the combined contrast waveform.

Preferably, the method in the light frequency changing step, a beam of far-ultraviolet laser light of the far-ultraviolet band is used as the beam of light of the predetermined frequency band.

Preferably, at least part of the inspected surface comprises the surface formed.

Preferably, the method further comprises a step of selecting and using light of a frequency band differing according to the type of the object to be inspected constituting the inspected surface for the light of the predetermined frequency band.

Alternatively, preferably, the method further comprises a step of selecting and using one of a beam of far-ultraviolet laser light of the far-ultraviolet band and a beam of visible laser light of the visible band for the light of the predetermined frequency band according to the type of the object to be inspected constituting the inspected surface.

More preferably, the method further comprises a step of using the beam of visible laser light for inspection of an inspected surface constituted by a material such as polycrystalline silicon having a relatively low spectral reflectance for light of a short wavelength and a step of using the beam of far-ultraviolet laser light for inspection of an inspected surface formed by a material having a relatively high spectral reflectance for light of a short wavelength.

Preferably, the inspected surface comprises the surface of a film stacked on a semiconductor substrate and formed into a predetermined pattern.

More preferably, the patterns are formed symmetrical about a predetermined center line, and a part which is not symmetrical about the center line in the combined contrast waveform data is detected as a defect.

Preferably, the method further comprises two-dimensionally making the beams of inspection light scan the inspected surface, generating a contrast image reflecting a three-dimensional shape of the inspected surface from the combined contrast waveforms obtained as a result of the scannings, and detecting a defect of the inspected surface based on the contrast image.

Preferably, the method further comprises two-dimensionally making the beams of inspection light scan the inspected surface, generating a contrast image reflecting a three-dimensional shape of the inspected surface from the combined contrast waveforms obtained as a result of the scannings, and detecting a defect of the inspected surface based on the contrast image.

According to a fifth aspect of the present invention, there is provided a defect inspection method for inspecting for a defect present in an inspected surface, comprising converting light of a predetermined frequency band to a beam of inspection light and a beam of reference light having close frequencies different from each other, focusing the beam of inspection light on the inspected surface to form a focal point and scanning it the inspected surface, superposing the beam of reflected light of the beam of inspection light from the inspected surface and the beam of reference light on each other to cause interference between them and detecting the intensity of the related superposed light by confocal detection, generating a contrast waveform in the scanning direction at the focal position based on the detected light intensity, and detecting a defect of the inspected surface based on the contrast waveform.

That is, in the present invention, light emitted from a light source is converted to a plurality of beams of inspection light and a beam of reference light having close frequencies different from each other by the light frequency changing means.

The plurality of beams of inspection light output from the light frequency changing means are focused on the inspected surface by the focusing means through the identical optical path. The focused beams of inspection light have frequencies different from each other, so a plurality of different focal points are formed with respect to the inspected surface. The focused beams of inspection light are made to scan the inspected surface by the scanning means, the beams of reflected light from the inspected surface are superposed on the beam of reference light by the superposing means, and a beat of the differential frequency is produced by the superimposition.

The beat of the differential frequency is detected by the light receiving means. The detection of the beat of the differential frequency generated by interference between these beams of inspection light and the beam of reference light is referred to as optical heterodyne detection. By the optical heterodyne detection, the contrast characteristic of the image to be obtained is improved, and an S/N ratio of the detection light is improved.

Further, when detecting the optical intensity by optical heterodyne detection, the light receiving means detects the intensity by confocal detection.

Confocal detection is a detection method for making the reflected light pass through a pinhole, slit, or other aperture and strike the light receiving surface of the light receiving means and detecting the intensity of part of a range including the center portion of the distribution of the intensity of the reflected light. The optical resolution is improved by the confocal detection, and the contrast characteristic of the obtained image is improved.

The intensity information of the reflected light obtained at the light receiving means by the optical heterodyne detection and the confocal detection includes intensity information of the reflected light obtained at a plurality of different focal positions, so the contrast waveform generating means generates contrast waveforms in the scanning direction at the focal positions and combines the generated contrast waveforms.

The combined contrast waveform is a combination of contrast waveforms obtained at a plurality of different focal positions, therefore even if there is a certain degree of unevenness in a depth direction in the surface shape of the inspected surface, a shape faithfully reflecting the surface shape of the inspected surface is exhibited.

A defect present in the inspected surface can be detected by the difference of the surface shape of the specified inspected surface from an intended shape based on the combined contrast waveform.

BRIEF DESCRIPTION OF THE DRAWINGS

The above object and features of the present invention will be more apparent from the following description of the preferred embodiments with reference to the accompanying drawings, wherein:

FIG. 4A is a view of an example of the combined contrast waveform when there is a defect in the pattern, and FIG. 4B is a view of the state when the combined contrast waveform is folded at the center line O and superposed;

DESCRIPTION OF THE PREFERRED EMBODIMENTS

Figure 1:
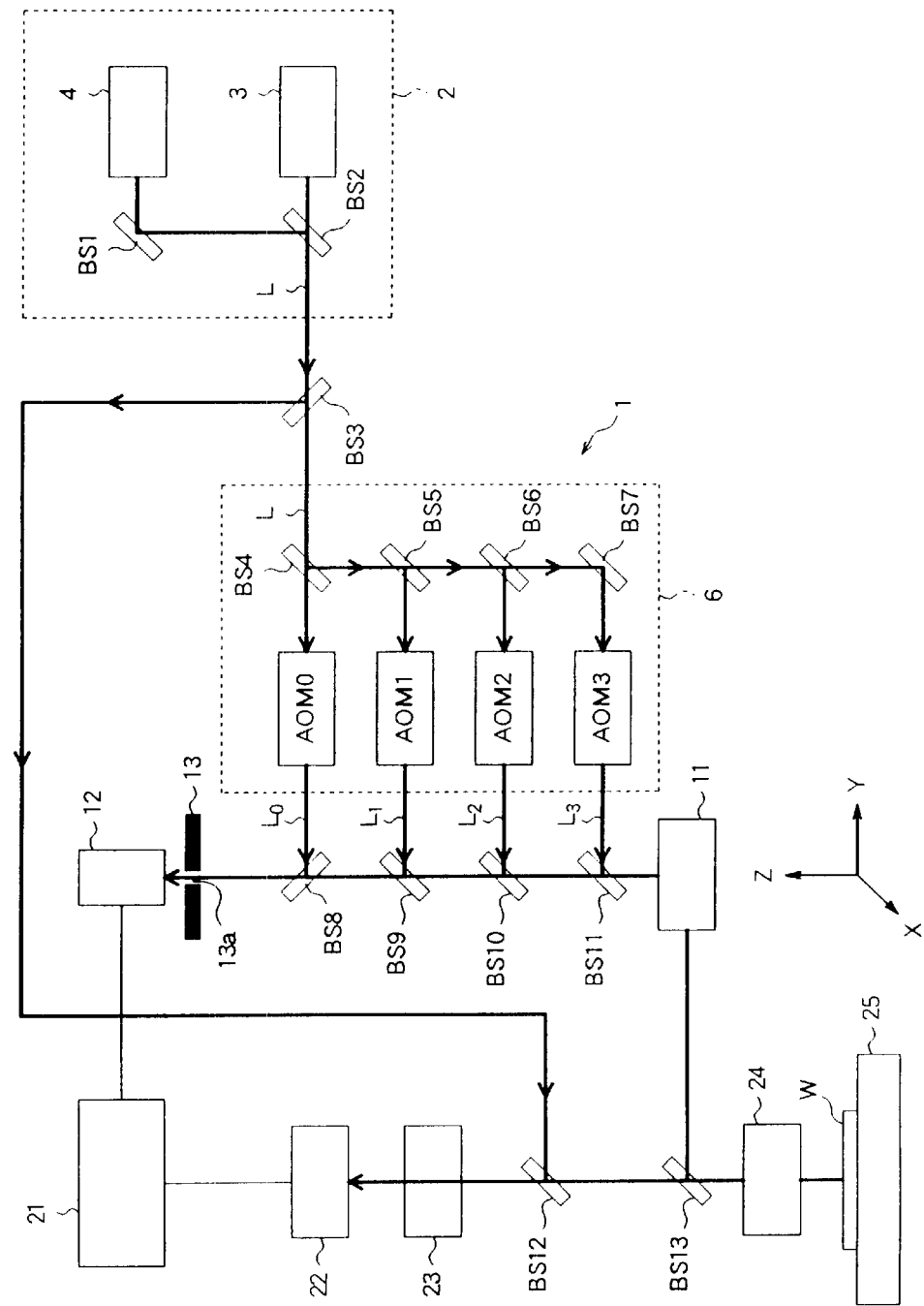
FIG. 1 is a view of the configuration of a defect inspection apparatus according to an embodiment of the present invention.

Below, an explanation will be made of a preferred embodiment of the present invention by referring to the drawings.

FIG. 1 is a view of the configuration of an embodiment of the defect inspection apparatus of the present invention.

A defect inspection apparatus 1 shown in FIG. 1 has a laser scanning type confocal microscope portion provided with a light source 2, a light frequency shifter unit 6 for shifting the frequency of the laser light, a laser scanning unit 11 for making the beam of laser light scan, an optical detection unit 12, a confocal pinhole plate 13, a camera unit 22, an image-forming lens 23, and an object lens 24 and a stage which holds an analyzing unit 21, the camera unit 22, the image-forming lens 23, and a wafer W as the object to be inspected and can control the positioning of the wafer W in an X-direction, Y-direction, and a Z-direction with a high precision.

The light source 2 has a far-ultraviolet laser light source 3 and a visible laser light source 4.

The far-ultraviolet laser light source 3 outputs the far-ultraviolet laser light of the far-ultraviolet band having a relatively short wavelength.

The visible laser light source 4 outputs the visible laser light of the visible band.

The laser light output from the far-ultraviolet laser light source 3 passes through a beam splitter BS2 provided in the light source 2 and is output to a predetermined optical path outside the light source 2.

The laser light output from the visible laser light source 4 is reflected at a beam splitter BS1 provided in the light source 2 to strike the beam splitter BS2, reflected at the beam splitter BS2, and output to a predetermined optical path outside the light source 2.

The light source 2 has a mechanism capable of selecting and emitting the visible laser light of the visible band and the far-ultraviolet laser light of the far-ultraviolet band having a relatively short wavelength according to the type, purpose of the inspection, etc. of the object to be inspected.

In the present embodiment, with laser light of a short wavelength of for example 400 nm or less, visible laser light having a relatively long wavelength is used for the inspection for a defect present in the pattern formed by a material having a low spectral reflectance, for example, polycrystalline silicon.

Even with laser light of a short wavelength of for example 400 nm or less in which the problem as described above does not occur, far-ultraviolet laser light having a high optical resolution and short wavelength is used for the inspection for a defect of an interconnection pattern formed by a material such as aluminum having a relatively high spectral reflectance.

The light frequency shifter unit 6 has acousto-optic modulators (AOM) AOM0, AOM1, AOM2, and AOM3 and beam splitters BS4 to BS7 which each split one of the beams of laser light output from the light source 2 and split into two by the beam splitter BS3 and make it strike upon the acousto-optic modulators AOM0, AOM1, AOM2, and AOM3.

The acousto-optic modulators AOM0, AOM1, AOM2, and AOM3 add supersonic waves of different frequencies to the incident beams of laser light L to shift the frequencies to close frequencies different from each other and output beams of laser light having frequencies different from each other.

The acousto-optic modulator AOM0 shifts the frequency of the beam of laser light L to convert it to the beam of reference light L0 and outputs this, but it is also possible to adopt a configuration which does not change the frequency of the beam of laser light L, passes it as it is, and makes the frequency of the reference light L0 the same frequency as that of the beam of laser light L.

The acousto-optic modulators AOM1, AOM2, and AOM3 shift the beam of laser light L in frequency to output the beams of inspection light L1, L2, and L3.

On the output side of the light frequency shifter unit 6, beam splitters BS8 to BS11 are provided corresponding to the acousto-optic modulators AOM0, AOM1, AOM2, and AOM3.

The beam splitter BS8 reflects the beam of reference light L0 output from the acousto-optic modulator AOM0 and makes it strike a confocal pinhole 13a of the confocal pinhole plate 13.

The beam splitters BS9 to BS11 reflect the beams of inspection light L1, L2, and L3 output from the acousto-optic modulators AOM1, AOM2, and AOM3 and make them strike the laser scanning unit 3 through the identical optical path.

Note that the beam splitters BS8 to BS11 pass the beams of reflected light output from the laser scanning unit 11 therethrough and make them strike the confocal pinhole 13a of the confocal pinhole plate 13.

The laser scanning unit 3 is exposed the beams of inspection light L1, L2, and L3 from the light frequency shifter unit 6 which are reflected at the beam splitters BS9 to BS11 and pass through the identical optical path and scans and outputs these beams of inspection light L1, L2, and L3.

The laser scanning unit 11 can be configured by for example a galvanomirror or supersonic light polarization element though the mechanism is not illustrated here.

The object lens 24 is provided so that its optical axis becomes perpendicular relative to the stage 25 and focuses the beams of inspection light L1, L2, and L3 output from the laser scanning unit 11 reflected by the beam splitter BS13 provided above the object lens 24 to form the focal points on the wafer W held on the stage 25.

Figure 2:
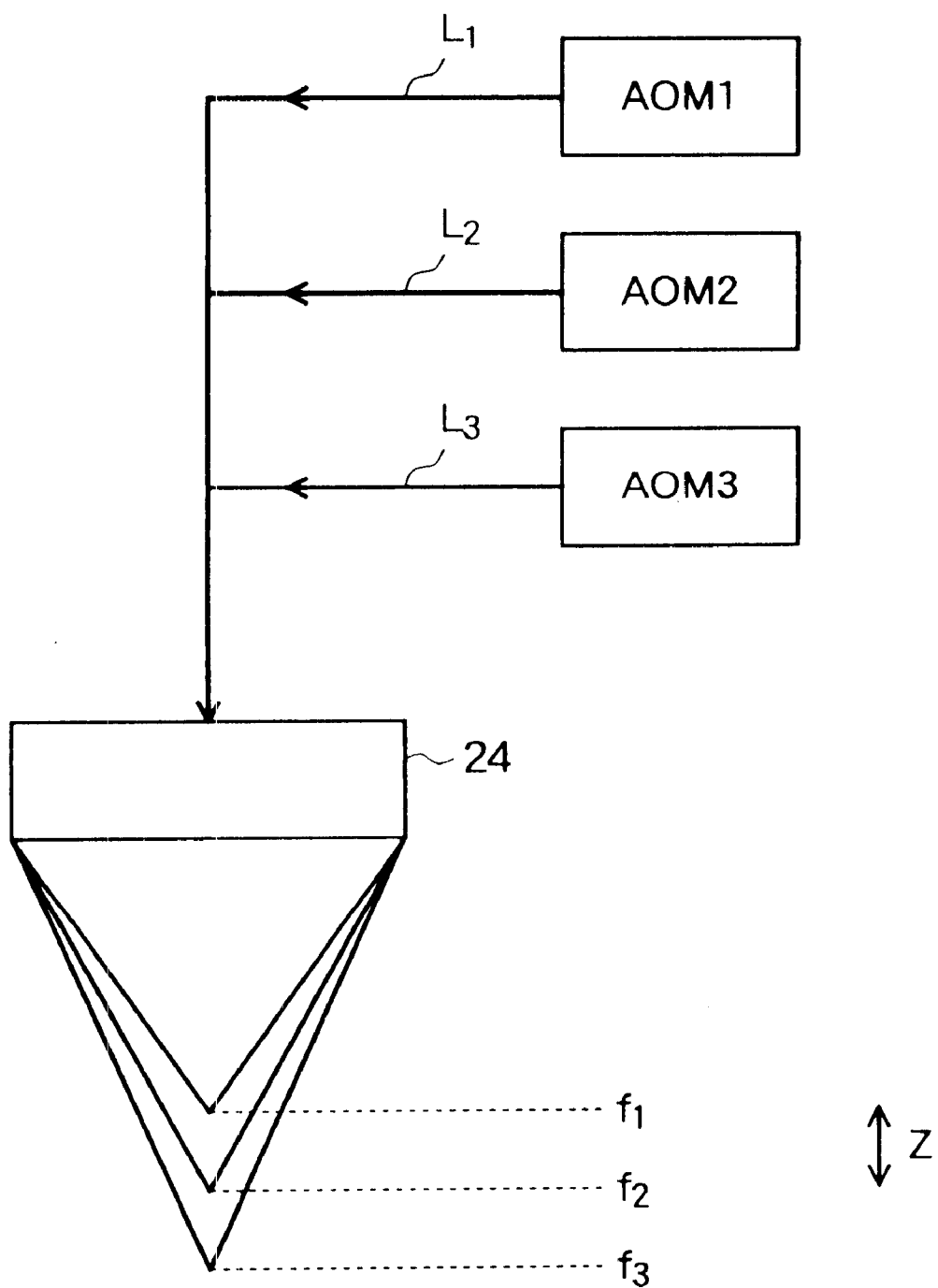
FIG. 2 is a view of the state where a plurality of beams of inspection light are focused by the object lens to form a plurality of different focal points.

The beams of inspection light L1, L2, and L3 output from the acousto-optic modulators AOM1, AOM2, and AOM3 have frequencies different from each other, therefore, for example, as shown in FIG. 2, the focal points of the beams of inspection light L1, L2, and L3 focused by the object lens 24 are formed at different focal positions f1, f2, and f3 in the Z-direction, that is, a height direction of the wafer W.

The optical detector 12 measures the intensity of the light obtained by superposing the beams of reflected light of the beams of inspection light L1, L2, and L3 striking the wafer W and the beam of reference light L0, converts this to an electric signal, and outputs the same to the analyzing unit 21.

The beams of reflected light of the beams of inspection light L1, L2, and L3 striking the wafer W follow the optical path of the beams of inspection light L1, L2, and L3 and strike the optical detector 12.

Namely, the beams of reflected light pass through the beam splitters BS11 to BS8 via the object lens 24, beam splitter BS13, and the laser scanning unit 11 to strike the optical detector 12. At this time, the beam of reference light L0 output from the acousto-optic modulator AOM0 also passes through the identical optical path as that for the beams of reflected light and strikes the optical detector 12, so the beam of reference light L0 and the beams of reflected light are superposed.

The optical detector 12 can be constituted by for example a photodiode.

The confocal pinhole plate 13 is formed with a confocal pinhole 13a as an aperture for confocal detection of the intensity of the superposed light by the optical detector 12 and is provided at a predetermined position relative to the optical detector 12.

The analyzing unit 21 generates the contrast waveforms along the scanning direction of the laser scanning unit 11 at focal positions f1, f2, and f3 on the wafer W based on the detection signal of the optical detector 12.

Further, the analyzing unit 21 combines the generated contrast waveforms at the focal positions f1, f2, and f3.

Further, the analyzing unit 21 detects a scratchy, dust, or other defect on the wafer W based on the combined contrast waveform. Note that the specific detection method of the analyzing unit 21 will be explained later.

The camera unit 22 is provided for observation of an illumination image obtained by the beam of laser light, in the laser light L emitted from the light source 2, which is split at the beam splitter BS3 and strikes the wafer W via the beam splitters BS12 and BS13 and the object lens 24 and an illumination image of a lamp etc.

The image-forming lens 22 is a lens for forming an image of the wafer W on the camera unit 22.

In the defect inspection apparatus 1 having the above configuration, for example, a wafer W having a stacked film structure is mounted on the stage 25. The wafer W is scanned by the beams of inspection light L1, L2, and L3 shifted in their frequencies at the light frequency shifter unit 6 by the laser scanning unit 11 and striking the wafer W via the object lens 24.

The beams of reflected light reflected at the wafer W pass through the confocal pinhole 13a of the confocal pinhole plate 13 together with the beam of reference light L0 shifted in its frequency at the light frequency shifter unit 6 via the object lens 24 and are received at the optical detection unit 12.

Namely, the defect inspection apparatus 1 performs optical heterodyne detection where the beams of reflected light reflected from the wafer W are superposed on the beam of reference light L0 and the beat of the superposed light (phenomenon where the intensity of the light changes by time by the differential frequency) at the optical detection unit 12.

Simultaneously, the superposed light passes through the confocal pinhole 13a for confocal detection.

Optical heterodyne detection is a method of detection of causing interference between two beams of laser light having different frequencies from each other, receiving this by the optical detector, generating the beat of the differential frequency produced by the superimposition of light waves having close frequencies, and measuring a distance from a phase change of this beat.

By using optical heterodyne detection, the contrast characteristic and the S/N ratio of the detection light can be improved.

In the defect inspection apparatus 1, use of optical heterodyne detection enables inspection with a very weak light and enables use of a far-ultraviolet laser light source 3 for the light source 2.

For this reason, for example, in the case when the object to be inspected is formed by a material such as a resist having a photosensitivity with respect to light, inspection to find defects in the surface of the material while preventing exposure of the photosensitive material by the very weak light becomes possible.

By using far-ultraviolet laser light having a short wavelength, the optical resolution can be improved.

Confocal detection is a detection method for making beams of reflected light pass through a pinhole, slit, or other aperture to receive the light and detecting the intensity of part of the range including the center portion of the distribution of intensity of the reflected light. The various types of light noise accompanying the reflected light are cut so as not to enter into the light receiving surface. Only the intensity in a so-called Airy disk is measured. Therefore the contrast characteristic of the image can be improved, and the optical resolution can be improved.

Next, an explanation will be made of an example of a method for inspection of a defect on a wafer W using a defect inspection apparatus 1 having the above configuration.

Referring to FIG. 3, an explanation will be given taking as an example a case, in a process of manufacture of a semiconductor device having a stacked film structure, of inspecting if there are minute defects in an aluminum interconnection pattern AP and a resist pattern RP on a pattern SP made of silicon oxide on a wafer W in an integrated circuit process, for example, the aluminum interconnection step.

First, the wafer W is mounted on the stage 25 of the defect inspection apparatus 1.

A predetermined alignment of the wafer W is carried out, and the stage 25 is moved to a predetermined position.

In this state, the beam of laser L is shifted in frequency to the beams of laser having close frequencies different from each other, and converted to the beams of incident light L0 and inspection light L1, L2, L3.

Next, the beams of inspection light L1, L2 and L3 shifted in frequency at the acousto-optic modulators AOM1, AOM2, and AOM3 of the light frequency shifter unit 6 pass the object lens 24 to expose the wafer W and form focal points at different focal positions f1, f2, and f3.

The beams of inspection light is scanned in the direction X by the laser scanning unit 11.

The beams of reflected light of the beams of the inspection light stroked and reflected by the wafer are superposed with the beam of the reference light L0.

The superposed light of the beams is passed the confocal pin-hole 13a, and detected the intensity of the superposed light of the beams by confocal detection by the light detection unit 12.

Next, the contrast waveforms in the scanning direction at the focal positions f1, f2, f3 based on the intensity of the superposed light of the beams detected by confocal detection by the light detecting unit 12.

Figures 3A, 3B, 3C, 3D:
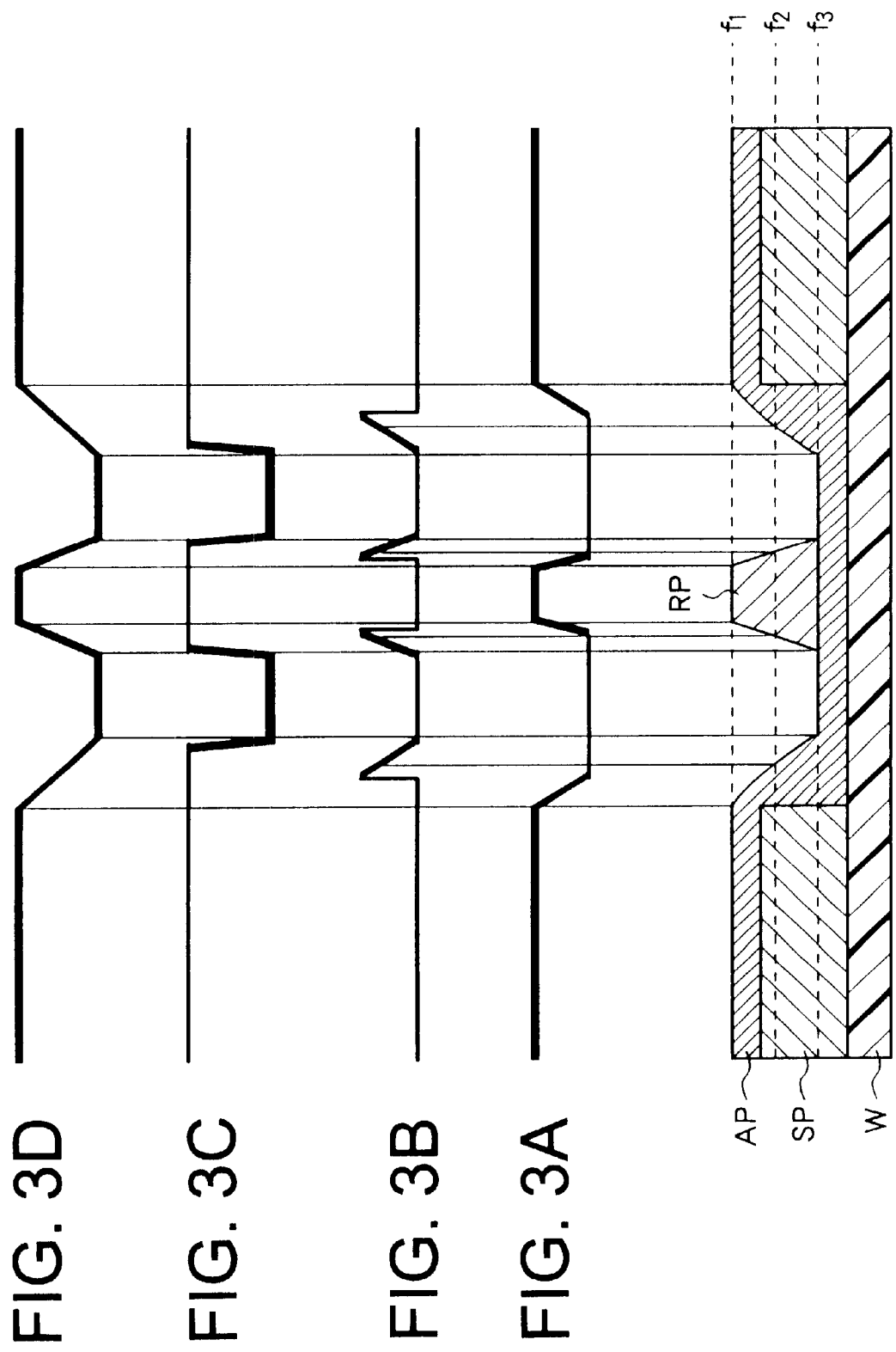
FIG. 3 is a view of the sectional structure of a pattern stacked on a wafer and an example of the contrast waveform generated in the analyzing unit 21.
Figure 5:
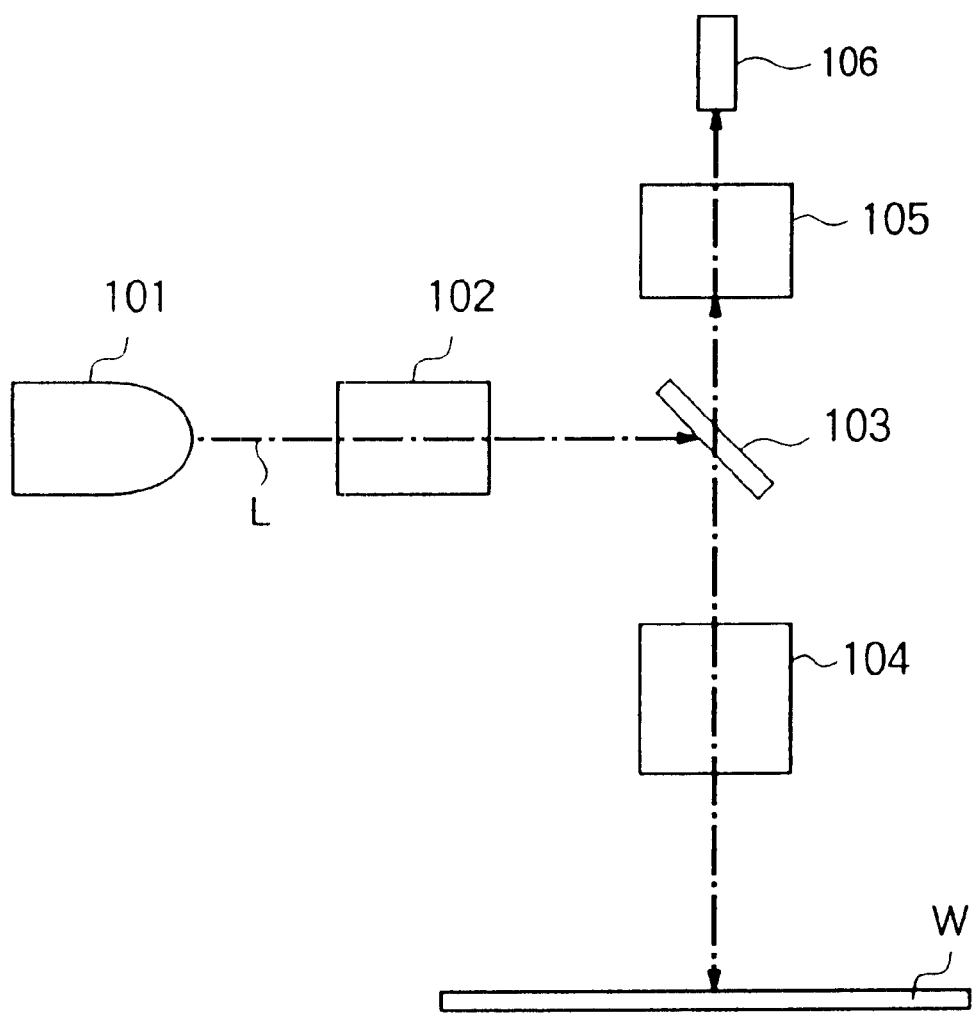
FIG. 5 is a view schematically showing the principal parts of the configuration of a defect inspection apparatus of a two-dimensional image for inspecting for a defect of patterns formed on the wafer.
Figures 6A, 6B:
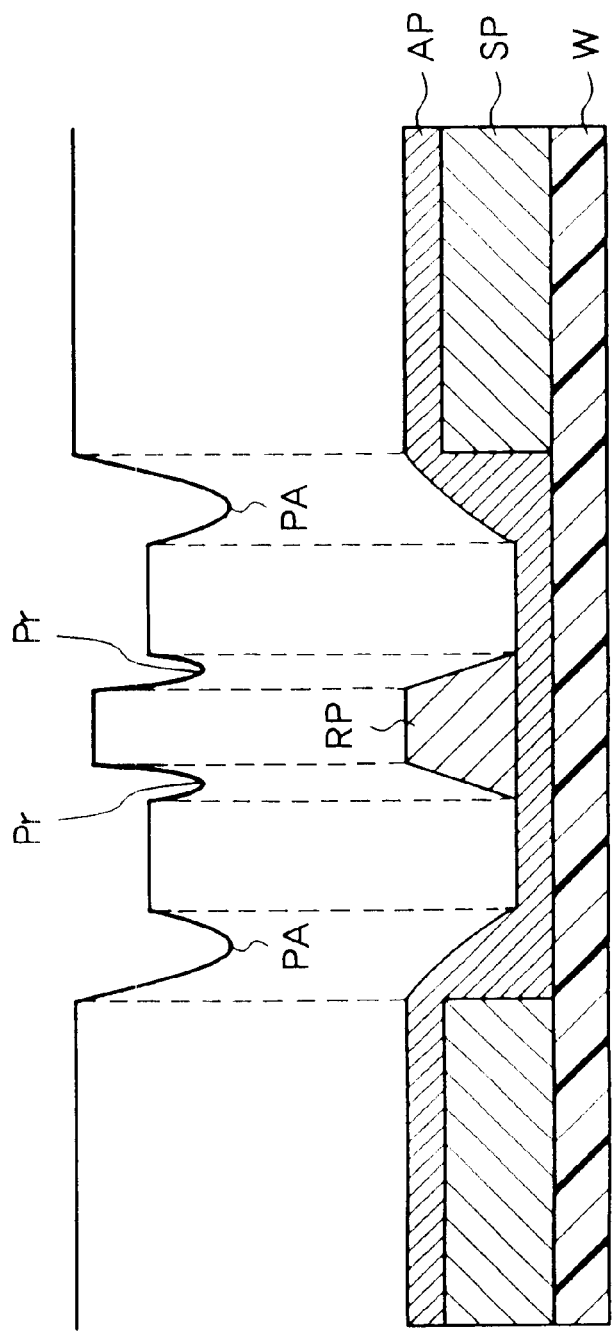
FIG. 6A is a sectional view of the process for manufacture of a semiconductor device having a stacked film structure.
FIG. 6B is a view of the contrast waveform thereof.

FIG. 3 shows the sectional structure of a pattern stacked on the wafer W and an example of the contrast waveform created at the analyzing unit 21, in which FIG. 3A shows the contrast waveform at the focal position f1, FIG. 3B shows the contrast waveform at the focal position f2, and FIG. 3C shows the contrast waveform at the focal position f3.

As seen from FIG. 3A to FIG. 3C, the contrast waveforms become waveforms reflecting the shapes in the vicinity of the focal positions f1, f2. and f3, but do not reflect the shapes at positions away from the focal positions f1, f2, and f3.

The correct three-dimensional shape of the stacked pattern on the wafer W cannot be specifically determined from the contrast waveforms.

In the analyzing unit 21, the contrast waveforms at the focal positions f1, f2, and f3 are combined.

FIG. 3D shows the contrast waveform obtained by combining the contrast waveforms at the focal positions f1, f2, and f3.

As seen from FIG. 3D, if the contrast waveforms at the focal positions f1, f2, and f3 are combined, a contrast waveform correctly reflecting the surface shape of the pattern stacked on the wafer W can be obtained.

As a result, it becomes possible to specifically determine the surface shape of the pattern stacked on the wafer W.

When there is a defect in the surface of the pattern stacked on the wafer W, for example, if there is a defect in the inclined surface of the step portion of for example a pattern AL, the combined contrast waveform becomes the waveform as shown in for example FIG. 4A.

In FIG. 4A, a defect portion K is formed in the combined contrast waveform corresponding to the defect in the inclined surface of the step portion of the pattern AL.

By confirming the defect portion K of the contrast waveform by for example the naked eye, the defect can be detected at the inclined surface of the step portion of the pattern AL.

Further, in the analyzing unit 21 of the defect inspection apparatus 1 according to the present embodiment, the defect K is detected by for example the following method.

The resist pattern RP and the aluminum pattern AP are formed linearly symmetrically about a predetermined center line O (center of the superimposition) as shown in FIGS. 4A and 4B.

In the analyzing unit 21 of the defect inspection apparatus 1, the combined contrast waveform data is folded at the center line focal O and superposed as shown in FIG. 4B.

There is no defect in the contrast waveform on the right side of the center line O, therefore a part K1 which is not symmetrical is generated in the contrast waveform superposed about the center line O.

The analyzing unit 21 of the defect inspection apparatus 1 detects this asymmetrical part K1 to detect the defect.

As described above, by the defect inspection apparatus 1 according to the present embodiment, the three-dimensional shape of the resist pattern RP and the aluminum pattern AP having a large step difference which could not be correctly measured by the defect inspection apparatus for a two-dimensional image of the related art can be correctly specified from the combined contrast waveform.

As a result, it becomes possible to detect a minute defect present in the wafer W surface on which the resist pattern RP and the aluminum pattern AP are formed based on the combined contrast waveform.

In the defect inspection apparatus 1 according to the present embodiment, the laser scanning unit 3 repeatedly performs the operation of making the beams of inspection light L1, L2, and L3 scan the surface of the wafer W in for example the X-axial direction and then moving the stage 25 by a predetermined amount in a Y-axial direction and making them scan again in the X-axial direction, whereby the beams of inspection light L1, L2, and L3 can be made to scan the surface of the wafer W two-dimensionally.

The analyzing unit 21 of the defect inspection apparatus 1 can also generate a contrast image reflecting the three-dimensional shape of the surface of the entire wafer W from the combined contrast waveform obtained as a result of the scannings in the two-dimensional scanning as described above.

By employing such a configuration, the defect inspection can be carried out while viewing the entire wafer W surface, therefore inspection becomes easy.

Further, in the present embodiment, the optical resolution is improved by the confocal detection, and real time three-dimensional measurement can be carried out by optical heterodyne detection and simultaneous detection at a plurality of focal positions.

Note that, in the above-mentioned embodiment, the light frequency shifter used three acousto-optic modulators, but if the number of this is increased, the precision of the contrast waveform can be improved.

For example, an acousto-optic deflector (AOD) and an acousto-optic modulator using a surface acoustic wave (SAW) can be used for the light frequency shifter unit 6.

The defect inspection apparatus 1 is not limited to the case of inspecting for a defect present in the resist pattern RP and the aluminum pattern AP in the aluminum interconnection step. It can be applied to cases of inspecting for defects of various patterns and films in semiconductor devices having a variety of stacked film structures in various steps.

According to the present embodiment, by providing the confocal pinhole plate 13 in the optical detector 12 and detecting the intensity of the reflected light by confocal detection, the optical resolution can be improved and the contrast characteristic can be improved.

By using optical heterodyne detection superposing the beams of inspection light and beam of reference light with different frequencies and detecting the beat of the differential frequency generated due to the interference between the beams of inspection light and the beam of reference light at the optical detector 12, the precision of the contrast waveform is improved and the S/N ratio of the light to be detected can be improved.

According to the present embodiment, by using optical heterodyne detection, even if relatively weak light is used as the laser light, a contrast waveform with a high precision is obtained, therefore, far-ultraviolet laser light having a relatively short wavelength can be used for the laser light, the optical resolution can be further improved, and even if very weak light is used, a contrast waveform with a high precision is obtained, therefore, a precise defect inspection of a material such as a resist having photosensitivity becomes possible.

Up to the present, in order to obtained a three-dimensional shape, for example, a plurality of two-dimensional images are acquired while moving a stage holding a wafer in the incident direction of the measurement use laser and these images are combined so as to combine a three-dimensional image. Due to this configuration, a long time is required for obtaining the three-dimensional shape and the precision of the obtained image is lowered since the stage is moved, but in the present embodiment, the three-dimensional shape can be instantaneously obtained and also the precision of the obtained image becomes high.

In the present embodiment, three acousto-optic modulators were used in the light frequency shifter unit 6 in order to create the beams of inspection light, but if the number is further increased, a further precise contrast waveform can be obtained and the precision of the defect inspection can be further improved.

Note that the present invention is not limited to the above embodiment.

For example, a configuration can be employed not using the confocal pinhole plate 13 and not performing confocal detection. In this case, the contrast characteristic is slightly lowered since confocal detection is not carried out, but the hardware configuration can be simplified.

In the above embodiment, different focal positions were formed on the wafer W by using a plurality of acousto-optic modulators AOM1 to AOM3, but it is also possible to employ for example a configuration for inspection by a single focal point without forming a plurality of focal points by using a single acousto-optic modulator AOM.

For example, when the surface shape of the wafer W has a relatively shallow step portion, a contrast waveform having an improved contrast characteristic by confocal detection and optical heterodyne detection can be obtained and the surface shape can be correctly specified.

Due to the present invention, not only inspection for defects present in the pattern of a semiconductor device of a stacked film structure, but also for example observation and defect inspection of the shape in a contact hole having a high aspect ratio, inner surface shape, and bottom of the contact hole are possible, thus the present invention can be applied to defect inspection of the inspected surfaces of a variety of objects having unevenness.

Summarizing the effects of the invention, according to the present invention, by using optical heterodyne detection, measurement with the very weak light becomes possible and a far-ultraviolet laser can be used for the light source.

According to the present invention, by forming a plurality of different focal points and finding the contrast waveforms at the focal positions, real time measurement of the three-dimensional shape becomes possible and also a shortening of the measurement time can be achieved.

According to the present invention, by repeating the inspection while moving a plurality of different focal points in a depth direction of the three-dimensional object to be inspected, high precision three-dimensional information can be obtained and the present invention can be applied to also three-dimensional image observation. For example, the observation and measurement of the bottom of a contact hole having a large aspect ratio are possible.

The defect inspection apparatus and method according to the present invention is effective not only to the defect inspection of the flat inspected surface but also the same of inspected surface with unevenness, differences in level or grooves.

What is claimed is:

1. A defect inspection apparatus for inspecting for a defect in an inspected surface, comprising:
    a light source emitting a beam of light of a predetermined frequency band;
    a light frequency changing means for receiving as its input the beam of light emitted from the light source and outputting the related beam of light converted to a plurality of beams of inspection light and a beam of reference light beam having close frequencies different from each other;
    a light focusing means upon which the beams of inspection light output from the light frequency changing means are incident through an identical optical path and focusing the related beams of inspection light to the inspected surface to form a plurality of different focal points corresponding to the beams of inspection light;
    a scanning means for scanning the focused beams of inspection light on the inspected surface;
    a superposing means for superposing the beam of the reflected light of the inspection light from the inspected surface and the beam of reference light to cause interference between the beams of reflected light and the beam of reference light;
    a confocal defecting means upon which the superposed light of the beams of reflected light and the beam of reference light is incident and detecting the intensity of the superposed light by confocal detection; and
    a contrast waveform generating means for generating contrast waveforms reflecting a surface shape of the inspected surface in the scanning direction at the focal positions in response to the light intensity detected by the confocal defecting means and combining the contrast waveforms.

2. A defect inspection apparatus as set forth in claim 1, further comprising a defect detecting means for detecting defects of the pattern based on the contrast waveforms.

3. A defect inspection apparatus as set forth in claim 1, wherein said confocal defecting means has:
    a pin hole aperture plate having a small aperture for passing the superposed light and a light receiving element and detecting the intensity of the superposed light passed said aperture.

4. A defect inspection apparatus as set forth in claim 1, wherein the light source selectively outputs a beam of visible laser light of a visible band and a beam of far-ultraviolet laser light of a far-ultraviolet band.

5. A defect inspection apparatus as set forth in claim 1, wherein the superposing means has beam splitters for reflecting the beam of reference light output from the light frequency changing means to the control defecting means, passing the beams of reflected light from the inspected surface striking it after following an identical optical path as that for the beams of inspection light, and exposing the same to the focal detecting means.

6. A defect inspection apparatus as set forth in claim 1, wherein the light frequency shifting means has a plurality of acousto-optic modulators means for changing the frequency of the light emitted from the light source by supersonic waves of different frequencies from each other.

7. A defect inspection apparatus as set forth in claim 1, wherein the inspected surface comprises uneven surface.

8. A defect inspection apparatus as set forth in claim 1, wherein the inspected surface comprises the surface of a film stacked on a semiconductor substrate and formed into a predetermined pattern.

9. A defect inspection apparatus as set forth in claim 8, wherein:
    the patterns are formed symmetrical about a predetermined center line and
    the defect detecting means detects a part which is not symmetrical about the center line in the contrast waveform data obtained by the contrast waveform generating means as a defect.

10. A defect inspection apparatus as set forth in claim 1, wherein the scanning means has a galvanomirror or a supersonic light polarization element for scanning the beams of inspection light on the inspected surface.

11. A defect inspection apparatus as set form in claim 1, wherein:

the scamming means two-dimensionally scans the beams of inspection light on the inspected surface and the surface shape of the inspected surface generated by the contrast waveform generating means is a contrast image reflecting a three-dimensional shape of the inspected surface from the combined contrast waveforms obtained as a result of the scannings.

12. A defect inspection apparatus for inspecting for a defect present in an inspected surface, comprising:

a light source for emitting a beam of light of a predetermined frequency band;

a light frequency changing means for receiving as its input the beam of light emitted from the light source and outputting the related beam of light converted to a plurality of beams of inspection light and a beam of reference light beam having close frequencies different from each other;

a light focusing means upon which the beams of inspection light output from the light frequency changing means are incident through an identical optical path and focusing the related beams of inspection light to the inspected surface to form a plurality of different focal points corresponding to the beams of inspection light;

a scanning means for making the focused beams of inspection light scan the inspected surface;

a superposing means for superposing beams of reflected light of the beams of inspection light from the inspected surface and the beam of reference light on each other to cause interference between the related beams of reflected light and the beam of reference light;

a light receiving means upon which the superposed light of the beams of reflected light and the beam of reference light is incident and detecting the intensity of the superposed light; and a contrast waveform generating means for generating contrast waveforms reflecting a surface shape of the inspected surface in the scanning direction at the focal positions based on the light intensity detected by the light receiving means and combining the contrast waveforms.

13. A defect inspector apparatus as set forth in claim 12, further comprising a defect detecting means for detecting a defect of a pattern based on the contrast waveforms.

14. A defect inspection apparatus as set forth in claim 12, wherein the inspected surface comprises the surface of a film stacked on a semiconductor substrate and formed into a predetermined pattern.

15. A defect inspection apparatus as set forth in claim 14, wherein:

the patterns are formed symmetrical about a predetermined center line and the defect detecting means detects a part which is not symmetrical about the center line in the contrast waveform data obtained by the contrast waveform generating means as a defect.

16. A defect inspection apparatus for inspecting for a defect present in an inspected surface, comprising:

a light source for emitting a beam of light of a predetermined frequency band;

a light frequency changing means for receiving as its input the beam of light emitted from the light source and outputting the related beam of light converted to a plurality of beams of inspection light and a beam of reference light beam having close frequencies different from each other;

a light focusing means for focusing the related beams of inspection light output from the light frequency changing means on the inspected surface to form focal points;

a scanning means for scanning the focused beams of inspection light on the inspected surface;

a superposing means for superposing the beam of reflected light of the beams of inspection light from the inspected surface and the beam of reference light on each other to cause interference between the beams of reflected light and the beam of reference light;

a confocal defecting means upon which the superposed light of the beams of reflected light and the beam of reference light is incident and detecting the intensity of the superposed light by confocal detection; and a contrast waveform generating means for generating contrast waveforms reflecting a surface shape of the inspected surface in the scanning direction at the focal positions based on the light intensity detected by the control defecting means.

17. A defect inspection apparatus as set forth in claim 16, further comprising a defect detecting means for detecting defects of the pattern based on the contrast waveforms.

18. A defect inspection apparatus as set forth in claim 16, wherein the inspected surface comprises the surface of a film stacked on a semiconductor substrate and formed into a predetermined pattern.

19. A defect inspection apparatus as set forth in claim 18, wherein:

the patterns are formed symmetrical about a predetermined center line and the defect detecting means detects a part which is not symmetrical about the center line in the contrast waveform data obtained by the contrast waveform generating means as a defect.

20. A defect inspection apparatus as set forth in claim 15, wherein said confocal defecting means has:

an aperture plate having a small aperture for passing the superposed light and a light receiving element for detecting the intensity of the superposed light passed said aperture.

* * * * *

UNITED STATES PATENT AND TRADEMARK OFFICE
CERTIFICATE OF CORRECTION

PATENT NO.     : 6,337,488 B1
DATED          : January 8, 2002
INVENTOR(S)    : Kouki Okawauchi It is certified that error appears in the above-identified patent and that said Letters Patent is hereby corrected as shown below:

<u>Column 15,</u>
Line 9, replace "scamming" with -- scanning --.

Signed and Sealed this

Fifth Day of November, 2002

*Attest:*

*Attesting Officer*

JAMES E. ROGAN
*Director of the United States Patent and Trademark Office*